United States Patent
Legrain-Raspaud et al.

(10) Patent No.: US 9,402,872 B2
(45) Date of Patent: Aug. 2, 2016

(54) PROBIOTIC STRAINS FOR USE IN IMPROVING TRANSEPITHELIAL RESISTANCE

(75) Inventors: Sophie Legrain-Raspaud, Limours (FR); Gianfranco Grompone, Paris (FR); Sandrine Capronnier, Villemoisson sur Orge (FR); Isabelle Chambaud, Issy les Moulineaux (FR); Biliana Lesic, Palaiseau (FR)

(73) Assignee: Compagnie Gervais Danone, Paris (FR)

( * ) Notice: Subject to any disclaimer, the term of this patent is extended or adjusted under 35 U.S.C. 154(b) by 0 days.

(21) Appl. No.: 13/700,482

(22) PCT Filed: May 30, 2011

(86) PCT No.: PCT/IB2011/052368
§ 371 (c)(1),
(2), (4) Date: Feb. 22, 2013

(87) PCT Pub. No.: WO2011/148358
PCT Pub. Date: Dec. 1, 2011

(65) Prior Publication Data
US 2013/0216510 A1    Aug. 22, 2013

(30) Foreign Application Priority Data

May 28, 2010   (WO) .................. PCT/IB2010/001536

(51) Int. Cl.
| | |
|---|---|
| C12N 1/20 | (2006.01) |
| A61K 35/747 | (2015.01) |
| A23L 1/30 | (2006.01) |
| A61K 35/74 | (2015.01) |
| A61K 35/745 | (2015.01) |

(52) U.S. Cl.
CPC ............. *A61K 35/747* (2013.01); *A23L 1/3014* (2013.01); *A61K 35/74* (2013.01); *A61K 35/745* (2013.01); *A23V 2002/00* (2013.01); *A23Y 2220/73* (2013.01); *A23Y 2300/55* (2013.01)

(58) Field of Classification Search
CPC .................................. C12N 1/20; C12R 1/225
See application file for complete search history.

(56) References Cited

U.S. PATENT DOCUMENTS

| | | | |
|---|---|---|---|
| 2006/0093592 A1* | 5/2006 | Cheruvanky et al. | 424/93.45 |
| 2008/0274085 A1* | 11/2008 | Daube et al. | 424/93.4 |
| 2010/0015111 A1* | 1/2010 | Magowan et al. | 424/93.45 |
| 2010/0061967 A1* | 3/2010 | Rautonen | 424/93.45 |

OTHER PUBLICATIONS

Klingberg, Application of Measurements of Transepithelial Electrical Resistance of Intestinal Epithelial Cell Monolayers to Evaluate Probiotic Activity, Applied and Environmental Microbiology, 71, pp. 7528-7530, 2005.
Nissen, Gut Health Promoting Activity of New Putative Probiotic/Protective *Lactobacillus* ssp. Strains: A Functional Study in the Small Intestinal Cell Model, International Journal of Food Microbiology, 135, pp. 288-294, 2009.

* cited by examiner

*Primary Examiner* — Ruth Davis
(74) *Attorney, Agent, or Firm* — Morgan, Lewis & Bockius LLP

(57) ABSTRACT

The invention relates to the use of lactic acid bacteria, for use in improving transepithelial resistance and more particularly in treating and/or preventing constipation and/or irritable bowel disease.

4 Claims, No Drawings

PROBIOTIC STRAINS FOR USE IN IMPROVING TRANSEPITHELIAL RESISTANCE

FIELD

The present application relates to compositions comprising strains of lactic acid bacteria for use in improving transepithelial resistance. Such compositions are especially suitable to treat and/or prevent constipation and/or irritable bowel disease.

BACKGROUND

Irritable bowel syndrome (IBS) or spastic colon is a functional bowel disorder characterized by chronic abdominal pain, discomfort, bloating, and alteration of bowel habits in the absence of any detectable organic cause. Diarrhoea or constipation may predominate, or they may alternate (classified as IBS-D, IBS-C respectively). IBS may begin after an infection (post-infectious, IBS-PI), a stressful life event or onset of maturity without any other medical indicators. In IBS, routine clinical tests yield no abnormalities, though the bowels may be more sensitive to certain stimuli, such as balloon insufflation testing.

IBS is a very common condition affecting approximately 15% of the population at any one time. There are about twice as many women as men with this condition. IBS is a source of chronic pain, fatigue and other symptoms, and it increases a patient's medical costs, and contributes to work absenteeism. Researchers have reported that the high prevalence of IBS, in conjunction with increased costs produces a disease with a high societal cost. It is also regarded as a chronic illness and can dramatically affect the quality of a sufferer's life.

Although there is at current no cure for IBS, there are treatments which attempt to relieve symptoms, including dietary adjustments, medication and psychological interventions.

Probiotics, in particular strains of lactic acid bacteria, have been reported to be beneficial in the treatment and/or prevention of IBS. Examples of such strains are disclosed in WO 2007/036230, WO 03/010297, and WO 2009/080800.

When disruption on intestinal mucosal barrier occurs, there is a leakage of water and plasma protein into the lumen and translocation of intestinal bacteria into the systemic circulation. These factors contribute typically to the development of local inflammations or even worse of systemic septicaemia. Bacterial LipoPolySaccharide (LPS) is known to cause mucosal hyperpermeability in vivo. LPS was found to promote gut barrier dysfunction through an oxidative mechanism and to lead to an increase in permeability which can be evaluated by measuring the difference in potential observed from the apical and basal sides of the monolayer, called the Trans Epithelial Electrical Resistance (TEER). Increasing evidence suggests that some probiotic and commensal bacteria ameliorate intestinal barrier impairment (decreasing the permeability) in vitro (Resta-Lenert and Barrett, 2006; Miyauchi et al., 2008) and in vivo, and help in relieving IBS and IBD symptoms. Lactobacilli and bifidobacteria were analyzed for this property (via TEER evaluation). It appears from this study that the increase of barrier resistance measured by TEER is strain dependant. There is a need for further strains that favor barrier integrity and/or decrease permeability, typically as evidence by TEER evaluations. There is a need for strains that improve such properties.

SUMMARY OF THE INVENTION

The invention addresses at least one of the needs above by providing a composition comprising at least one strain of bacteria selected from the group consisting of lactobacilli and bifidobacteria for use in increasing Trans Epithelial Electric Resistance (TEER) of intestinal epithelial cells, wherein said strain is selected from the group consisting of DN_116_0044 (CNCM I-4316 filed May 19, 2010) and DN_154_0062 (CNCM I-4319 filed May 19, 2010).

The invention also relates to a composition comprising at least one strain of bacteria selected from the group consisting of strains DN_116_0044 (CNCM I-4316 filed May 19, 2010) and DN_154_0062 (CNCM I-4319 filed May 19, 2010) for use in:

treatment and/or prevention of an intestinal disorder, preferably treatment and/or prevention of an intestinal permeability disorder, or treatment and/or prevention of a disorder selected from the group consisting of IBS, IBD and intestinal infection, or treatment and/or prevention of disorders found in elderly people, infants, or obese people.

The invention also relates to a composition comprising at least one strain of bacteria selected from the group consisting of strains DN_116_0044 (CNCM I-4316 filed May 19, 2010) and DN_154_0062 (CNCM I-4319 filed May 19, 2010), for use in administration to subjects suffering of a disorder selected from the group consisting of IBD, and IBS.

The invention also relates to a strain of lactic acid bacteria selected from the group consisting of DN_116_0044 (CNCM I-4316 filed May 19, 2010) and DN_154_0062 (CNCM I-4319 filed May 19, 2010). The invention also relates to compositions comprising such a strain.

According to one aspect the invention concerns a composition as mentioned above for use in decreasing intestinal permeability.

DETAILED DESCRIPTION

Definitions

In the present application the use of a compound or a composition is intended to cover the use itself, optionally with the connected intention, but also any communication associated to the compound or composition with commercial or legal consequences, for example advertisement, instructions or recommendation on the package of the compositions, instructions or recommendation on commercial support such as leaflets, brochures, posters, documentation filed in support to regulatory registrations for safety purpose, efficacy purpose, or consumer protection, for example at administrations such as EFSA in Europe.

In the present application the term "or" is not exclusive.
Strains of Bacteria

The strains of bacteria of the invention are lactobacilli or bifidobacteria, selected from DN_116_0044 (CNCM I-4316 filed May 19, 2010) and DN_154_0062 (CNCM I-4319 filed May 19, 2010).

All the herein referred bacterial strains have been deposited, according to the Budapest Treaty, before CNCM (Collection Nationale de Cultures de Microorganismes, 25 rue du Docteur Roux, Paris) as an International depositary authority.

The present invention also encompasses the use of the above mentioned strains, but also mutant strains or genetically transformed strains derived from any one of the parent strains, preferably still having activity on TEER. These mutant or genetically transformed strains can be strains wherein one or more endogenous gene(s) of the parent strain has (have) been mutated, for instance to modify some of its metabolic properties (e.g. its ability to ferment sugars, its resistance to acidity, its survival to transport in the gastrointestinal tract, its post-acidification or its metabolite production). They can also be strains resulting from the genetic transformation of the parent strain by one or more gene(s) of interest, for instance in order to give to said strain additional physiological features, or to allow it to express proteins of therapeutic or vaccinal interest that one wishes to administer through said strains.

Compositions

In the compositions of the invention, said strains can be used in the form of whole bacteria which may be living or not. Alternatively, they can be used in the form of a bacterial lysate or in the form of bacterial fractions; the bacterial fractions suitable for this use can be chosen, for example, by testing their properties on TEER. Preferably the bacterial cells are present as living, viable cells.

The compositions of the invention can be in any form suitable for administration, in particular oral administration. This includes for instance solids, semi-solids, liquids, and powders. Liquid composition are generally preferred for easier administration, for instance as drinks.

The composition can for example comprise at least $10^5$ cfu, preferably at least $10^6$ cfu, per g dry weight, of at least one strain of bacteria, preferably of strains of bacteria as mentioned above. These are preferably selected from the group consisting of lactobacilli and bifidobacteria.

When the bacteria are in the form of living bacteria, the composition may typically comprise $10^5$ to $10^{13}$ colony forming units (cfu), preferably at least $10^6$ cfu, more preferably at least $10^7$ cfu, still more preferably at least $10^8$ cfu, and most preferably at least $10^9$ cfu per g dry weight of the composition. In the case of a liquid composition, this corresponds generally to $10^4$ to $10^{12}$ colony forming units (cfu), preferably at least $10^5$ cfu, more preferably at least $10^6$ cfu, still more preferably at least $10^7$ cfu, and most preferably at least $10^9$ cfu/ml.

Examples of the compositions of the invention are nutritional compositions, including food products and in particular dairy products.

The composition can be for example a dairy product, preferably a fermented dairy product. The administration in the form of a fermented dairy product has the additional advantage of low lactose levels, which is further beneficial for IBS. Optionally, other strains of lactic acid bacteria may be present. The fermented product can be present in the form of a liquid or present in the form of a dry powder obtained by drying the fermented liquid. Preferably the fermented product is a fresh product. A fresh product, which has not undergone severe heat treatment steps, has the advantage that bacterial strains present are in the living form. Preferably the fermented product is a dairy product, more preferably fermented milk and/or fermented whey. Preferably the nutritional composition is a yoghurt, or a fermented milk in set, stirred or drinkable form. Preferably the fermented product is a cheese. Preferably the fermented product is a fermented vegetable, such as fermented soy, cereals and/or fruits in set, stirred or drinkable forms.

Preferably the present nutritional composition is a baby food, an infant milk formula or an infant follow-on formula. Preferably the present composition is a nutraceutical or a pharmaceutical product, a nutritional supplement or medical food.

Nutritional compositions of the invention also include food supplements, and functional food. A "food supplement" designates a product made from compounds usually used in foodstuffs, but which is in the form of tablets, powder, capsules, potion or any other form usually not associated with aliments, and which has beneficial effects for one's health. A "functional food" is an aliment which also has beneficial effects for one's health. In particular, food supplements and functional food can have a physiological effect—protective or curative—against a disease, for example against a chronic disease.

EXAMPLE 1

Teer Evaluations of Some Strains of Bacteria

The culture suspensions were washed with PBS. Subsequently, the bacteria (100 cfu/cell) were added to the apical side of the T84 cell monolayers. 96 strains were tested in the assay, including 64 Bifidobacteria and 32 Lactobacilli. After 2 h incubation, LPS (L4516, -EPEC-0127: B8) was added on the apical side at 40 ng/ml or not added. Then, after 2 h and 4 h incubation, the TEER value was measured to assess epithelial barrier function. All experiments were performed three times independently and in triplicate in presence and in absence of LPS. The value of the T84 at t=0 was set at 100%. In the absence of LPS TEER at T4 was 98.7% and at T6 100.2% In the presence of LPS the control T84 at T4 was 56.2% compared to t=0; At T6 the T84 control was 46.7%.

The results showed that strains increasing significantly epithelial integrity as measured by TEER both in presence and in absence of damaging LPS were very rare. One *L. rhamnosus*, DN_116_0044 (CNCM I-4316 filed May 19, 2010), as well as one *B. bifidum*, DN_154_0062 (CNCM I-4319 filed May 19, 2010), were identified to present improved TEER properties. Benchmarks such as NCC2705 and BB536 did not show significant improvements.

TABLE 1

TEER results of selected bacteria showing the best results (in damaging conditions)

| Strain | | TEER T4/TEER T0 in damaging conditions (LPS) | | TEER T6/TEER T0 in damaging conditions (LPS) | |
|---|---|---|---|---|---|
| | | Significance | Empiric mean | Significance | Empiric mean |
| T84 control | | | 56.20 | | 46.76 |
| DN_116_0044 (CNCM I-4316 filed May 19, 2010) | *L. rhamnosus* | ** | 56.25 | ** | 55.36 |
| NCC2705 (described in U.S. Pat. No. 7,183,101) | *B. longum* | Non significant | 56.25 | Non significant | 43.8 |
| BB536 | *B. longum* | *** | 50.59 | * | 42.02 |
| DN_154_0062 (CNCM I-4319 filed May 19, 2010) | *B. bifidum* | *** | 85.04 | *** | 75.40 |

*** p value <0.01;
** p value <0.05;
* p value <0.1

TABLE 2

TEER results of selected bacteria showing the best results
(in non damaging conditions)

| Strain | | TEER T6/TEER T0 in non damaging conditions (no LPS) | |
|---|---|---|---|
| | | Significance | Empiric mean |
| T84 | | | 100 |
| DN_116_0044 (CNCM I-4316 filed May 19, 2010) | L. rhamnosus | *** | 110 |
| DN_154_0062 (CNCM I-4319 filed May 19, 2010) | B. bifidum | *** | 134 |

*** p value <0.05

The invention claimed is:

1. A fermented dairy product comprising at least one isolated strain of lactic acid bacteria, as an active ingredient capable of increasing Trans Epithelial Electric Resistance (TEER) of intestinal epithelial cells following administration to a subject selected from the group consisting of *Lactobacillus rhamnosus* DN_116_0044 deposited under Accession No. I-4316 with Collection Nationale de Cultures de Micro-organismes on May 19, 2010 and *Bifidobacterium bifidum* DN_154_0062 deposited under Accession No. I-4319 with Collection Nationale de Cultures de Micro-organismes on May 19, 2010.

2. The fermented dairy product according to claim 1, wherein the fermented dairy product comprises at least $10^5$ cfu of at least one strain of bacteria selected from the group consisting of *Lactobacillus rhamnosus* DN_116_0044 and *Bifidobacterium bifidum* DN_154_0062, per gram dry weight.

3. The fermented dairy product according to claim 1, wherein the fermented dairy product comprises at least $10^6$ cfu of at least one strain of bacteria selected from the group consisting of *Lactobacillus rhamnosus* DN_116_0044 and *Bifidobacterium bifidum* DN_154_0062, per gram dry weight.

4. The fermented dairy product according to claim 1, wherein the fermented dairy product is yogurt.

* * * * *